United States Patent
Goodnough et al.

(10) Patent No.: US 6,670,322 B2
(45) Date of Patent: Dec. 30, 2003

(54) METHOD OF TARGETING PHARMACEUTICALS TO MOTOR NEURONS

(75) Inventors: Michael C. Goodnough, Stoughton, WI (US); Eric A. Johnson, Madison, WI (US); William H. Tepp, Stoughton, WI (US); Carl J. Malizio, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/870,262

(22) Filed: May 30, 2001

(65) Prior Publication Data

US 2003/0147921 A1 Aug. 7, 2003

Related U.S. Application Data

(60) Provisional application No. 60/208,516, filed on Jun. 1, 2000.

(51) Int. Cl.$^7$ .......... A61K 47/48; A61K 39/08; C07K 17/06
(52) U.S. Cl. .......... 514/2; 424/197.11; 530/350
(58) Field of Search .......... 514/2, 423; 424/197.11; 530/350

(56) References Cited

U.S. PATENT DOCUMENTS

| | | | | |
|---|---|---|---|---|
| 5,057,313 A | * | 10/1991 | Shih et al. | 424/85.91 |
| 5,939,070 A | * | 8/1999 | Johnson et al. | 424/194.1 |
| 6,203,794 B1 | * | 3/2001 | Dolly et al. | 424/184.1 |

* cited by examiner

*Primary Examiner*—Gary Kunz
*Assistant Examiner*—Ruixiang Li
(74) *Attorney, Agent, or Firm*—Quarles & Brady LLP

(57) ABSTRACT

A method of targeting therapeutic molecules to motor neurons is disclosed. In one embodiment, this method comprises the steps of (a) synthesizing a prodrug comprising a therapeutic molecule covalently bound to a polymeric delivery vehicle, and (b) conjugating the prodrug to a botulinum neurotoxin heavy chain.

11 Claims, 14 Drawing Sheets

Fig. 1. SDS-PAGE of purified type A neurotoxin (lane 1, unreduced; lane 2, reduced), light chain (lane 3), and heavy chain (lane 4).

Figure 2. Covalent modification of free thiol groups in type A botulinum neurotoxin.

Figure 3. Separation and purification of thiol modified type A botulinum heavy chain.

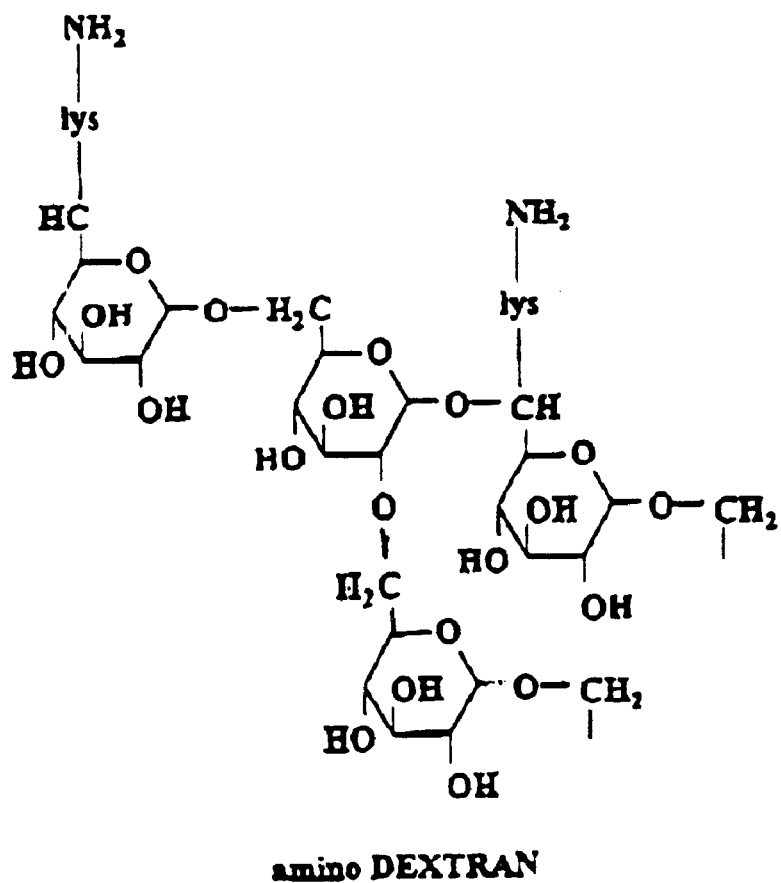
Figure 4. Structure of amino-dextrans.

Sulfosuccinimidyl-6-[alpha-methyl-alpha(2-pyridyldithio)-toluamido]hexanoate
Sulfo-LC-SMPT Figure 6. sulfo-LC-SMPT activated dextran.

Figure 7. Release of 2-thiopyridine leaving group from sulfo-LC-SMPT activated dextran.

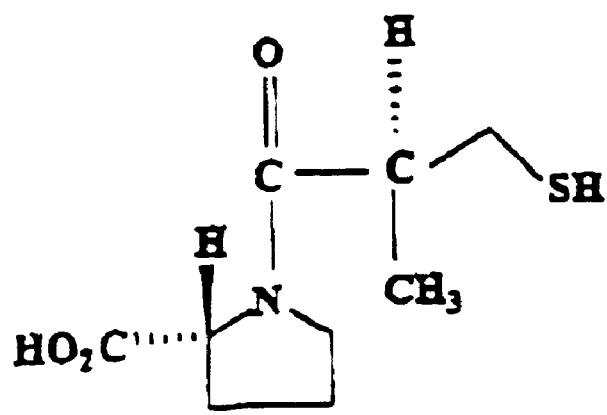
Figure 9. Structure of captopril.

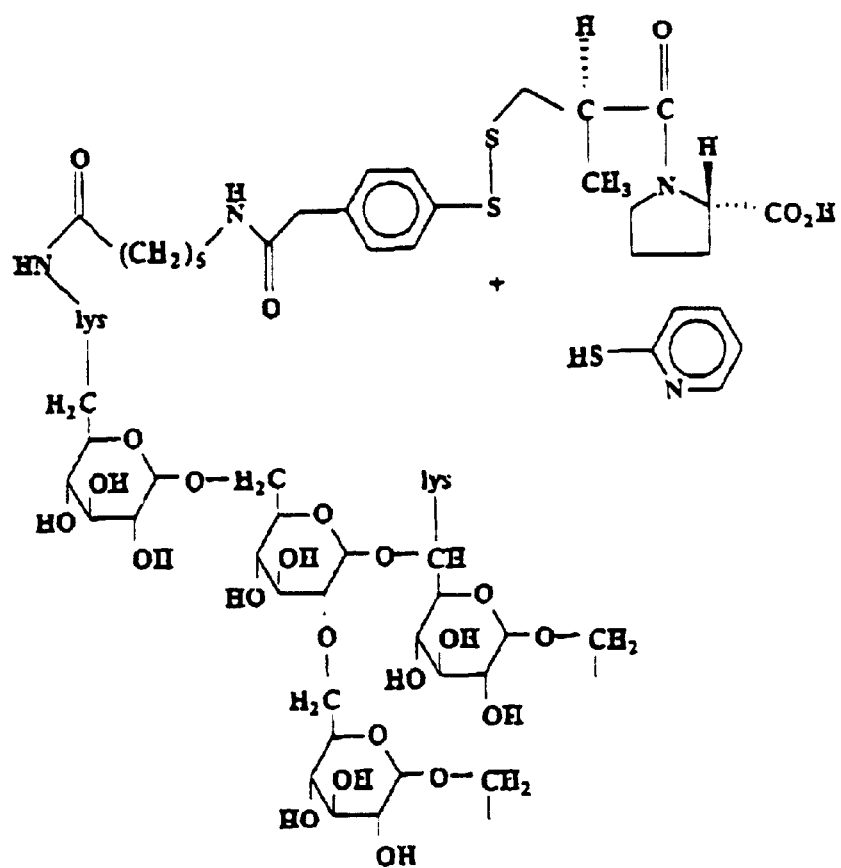
Figure 10. Captopril bound to functionalized amino-dextran.

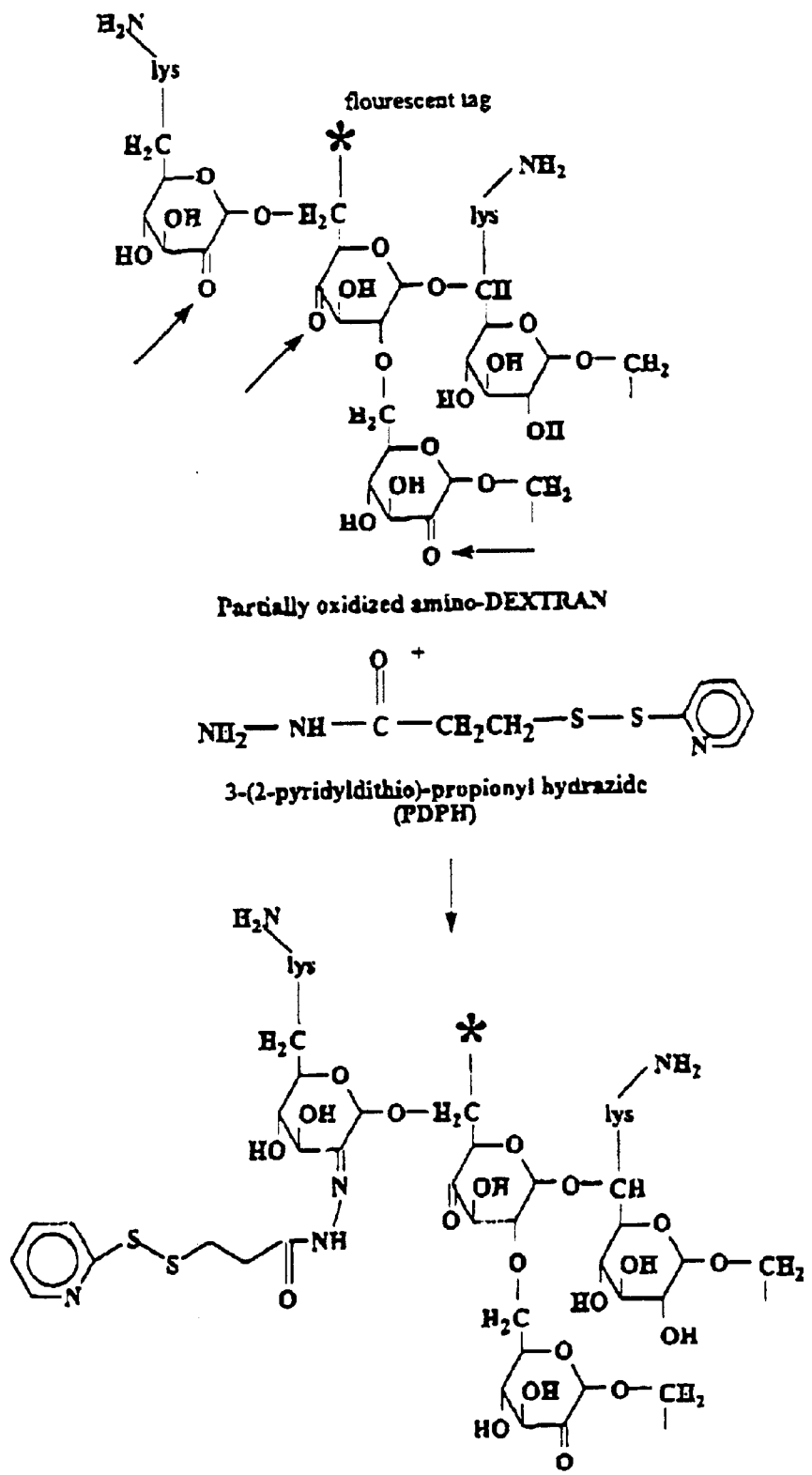
Figure 11. Oxidation of hydroxyl groups to carbonyl groups and subsequent reaction with PDPH.

I. amino-dextran ⇌⟶ carbonyl intermediate ⟶ thiol-reactive dextran
   ↑                                ↑
   sodium periodate                PDPH II. thiol-reactive dextran + captopril ⟶ amino-dextran prodrug
                                         ↘
                                          pyridine-2-thione III. amino-dextran prodrug + sulfo-LC-SMPT ⟶ thiol-reactive prodrug ↗ pyridine-2-thione
IV. thiol-reactive prodrug + botulinum heavy chain ⟶
                                          heavy chain/polymer prodrug
                                          conjugate Figure 12. Overall reaction scheme for conjugation of prodrug to botulinum heavy chain.

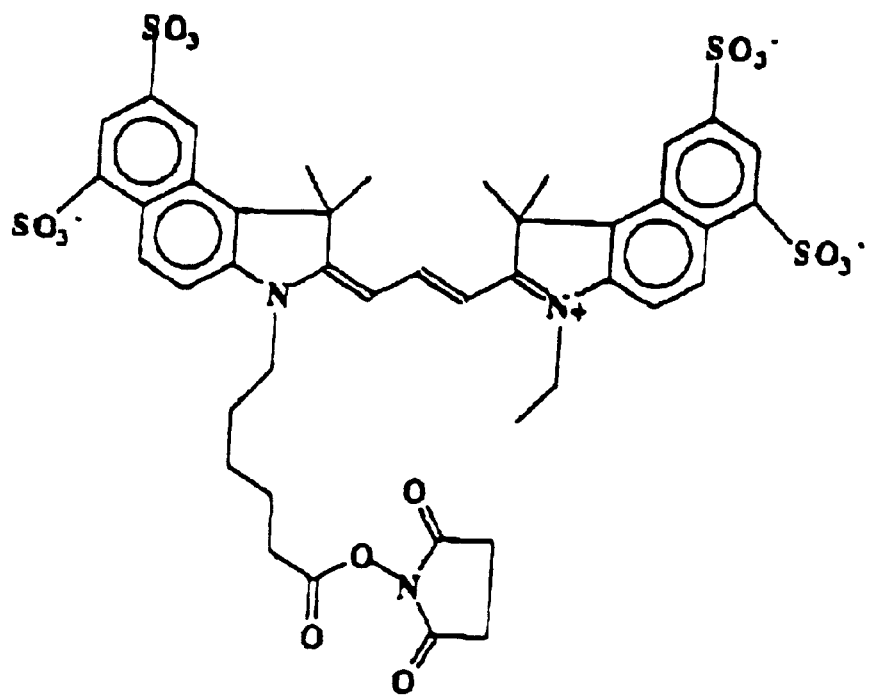
Fig. 13. Cy 3.5 monofunctional dye molecule. Molecular weight 1102. Absorbance max = 581 nm. Emission max = 596 nm.

METHOD OF TARGETING PHARMACEUTICALS TO MOTOR NEURONS

CROSS-REFERENCE TO RELATED APPLICATION

This application claims priority to U.S. Ser. No. 60/208,516, filed Jun. 1, 2000, which is incorporated by reference herein.

STATEMENT REGARDING FEDERALLY SPONSORED RESEARCH OR DEVELOPMENT

BACKGROUND OF THE INVENTION

Botulinum neurotoxin is an ongoing public health problem and is considered to be a potentially serious biological warfare agent. Recent worldwide events including the discovery of stockpiles of materials for manufacture of the toxin by extremist groups in Japan and Iraq have shown that the danger exists for biological terrorism. Intoxication from the toxin by consumption in food or water or from inhalation can lead to prolonged paralysis, incapacitation, and need for intensive supportive care. Depending on the route of administration, death can result from exposure to less than a microgram of toxin. There are no effective therapies once symptoms of botulism appear other than supportive treatments such as intubation and ventilation.

Within the last five years a number of potential therapies have been identified (e.g. aminoquinolines, metalloprotease inhibitors, aminopyridines. Adler, et al., 1996), and zinc chelators such as TPEN (Adler, et al., 1997). None of these are likely to work in vivo due to difficulty in penetration into the neuronal cytosol and high systemic toxicity. Although better metalloprotease inhibitors have recently been developed at the University of Wisconsin-Madison (Dr. Daniel Rich), these are likely to be limited by the same problems of membrane penetration and toxicity as the first generation of drugs. Anything that crosses lipid membranes easily will also be likely to cross the blood-brain barrier and have CNS toxicity. Any potential therapeutic compound that cannot be internalized into the nerve terminal cytosol will not be capable of antagonizing the active component of botulinum neurotoxin.

BRIEF SUMMARY OF THE INVENTION

In one embodiment, the present invention is a method of targeting therapeutic molecules to motor neurons. This method preferably comprises the step of (a) synthesizing a prodrug comprising a therapeutic molecule covalently bound to a polymeric delivery vehicle and (b) conjugating the prodrug to a botulinum neurotoxin heavy chain. In a preferred method of the present invention, the prodrug comprises at least two copies of the therapeutic molecule.

In another preferred method of the present invention, the botulinum neurotoxin heavy chain is type A botulinum neurotoxin and the therapeutic molecule is a metalloprotease inhibitor.

It is an object of the present invention to target therapeutic molecules to motor neurons.

Other objects, features and advantages of the present invention will become apparent after one has reviewed the specification, claims and drawings.

BRIEF DESCRIPTION OF THE SEVERAL VIEWS OF THE DRAWINGS

FIG. 1. SDS-PAGE of purified type A neurotoxin (lane 1, unreduced; lane 2, reduced), light chain (lane 3), and heavy chain (lane 4).

FIG. 2. Covalent modification of free thiol groups in type A botulinum neurotoxin.

FIG. 3. Separation and purification of thiol modified type A botulinum heavy chain.

FIG. 4. Structure of amino-dextrans.

FIG. 9. Structure of captopril.

FIG. 10. Captopril bound to functionalized amino-dextran.

FIG. 11. Oxidation of hydroxyl groups to carbonyl groups and subsequent reaction with PDPH.

FIG. 12. Overall reaction scheme for conjugation of prodrug to botulinum heavy chain.

FIG. 13. Cy 3.5 monofunctional dye molecule. Molecular weight 1102. Absorbance max=581 nm. Emission max=596 nm.

DETAILED DESCRIPTION OF THE INVENTION

Our solution to the above-stated problem is to use a modified, nontoxic form of the botulinum neurotoxin molecule to specifically target and deliver currently identified therapeutics as well as compounds developed in the future to the appropriate cholinergic motor neuron terminals. Once delivered to the presynaptic motor neuron membrane, the chimeric delivery vehicle preferably consisting of the heavy chain of the neurotoxin covalently linked with a polymeric molecule capable of delivering multiple copies of therapeutic compounds will bring the desired therapeutic across the membrane and into the neuron where the drug will be an effective therapeutic. In one embodiment, the drug may be an antagonist of botulinum neurotoxin. In another embodiment, the drug is an enzymatic inhibitor, including peptide inhibitors.

In one embodiment, the present invention is a method of targeting pharmaceuticals to motor neurons, comprising a first step of synthesizing prodrugs comprising at least one copy, and preferably multiple copies, of a therapeutic molecule (the Examples below describe the model metalloprotease inhibitor captopril as a therapeutic molecule) covalently bound to a polymeric delivery vehicle. The second step comprises conjugating the prodrug to the heavy chain of botulinum neurotoxin, preferably type A. This combination will yield a pharmaceutically active compound that specifically targets and internalizes desired substances into cholinergic neurons including active inhibitors of the active fragment of the neurotoxin itself.

We envision that the method of the present invention will be suitable for all heavy chains of botulinum neurotoxin. The Examples below describe a preparation using type A heavy chain. Other heavy chains (i.e., all seven serotypes of heavy chains, A–G) can be prepared in a similar manner. One may obtain the heavy chain in a variety of manners. Preferably, one will obtain heavy chains as described below in the Examples. In another embodiment of the present invention, one will obtain the heavy chain via recombinant DNA methods.

Polymeric delivery vehicle is an inert carrier molecule ranging in size from 10–40 kD that can be chemically modified such that therapeutic molecules may be covalently linked to it.

The polymeric delivery vehicle preferably comprises amine reactive dextran, described below as having a molecular weight of approximately 10 kD and 40 kD. Other suitable polymers include polyethylene glycol and polyimines.

Figure 5:
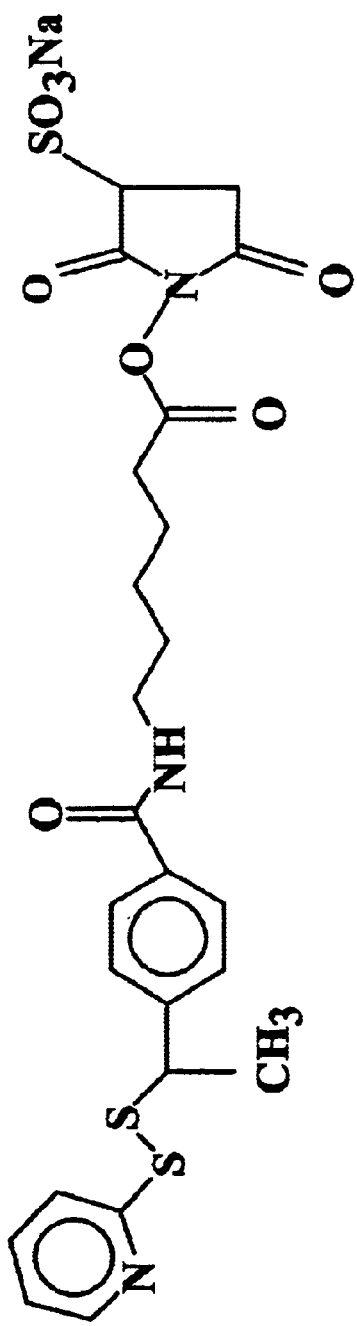
FIG. 5. Structure of the heterobifunctional linker sulfosuccinimidyl-6-[alpha-methyl-alpha(2-pyridythio)-toluamido]hexanoate (sulfo-LC-SMPT).

Dextran amines were preferably functionalized for conjugation with model inhibitors by addition of the water soluble heterobifunctional linker sulfosuccinimidyl-6-[alpha-methyl-alpha(2-pyridylthio)-toluamido]hexanoate (sulfo-LC-SMPT, FIG. 5). Other suitable linkers include heterobifunctional linkers containing amine and sulfhydryl reactive elements. Also useful are heterobifunctional linkers that are carboxy reactive as well as sulfhydral reactive.

The conjugation of the prodrugs to the heavy chain of botulinum neurotoxin will typically take place as follows:

We envision two preferable approaches to the synthesis of prodrugs that contain high molar concentrations of model inhibitor and have a traceable label.

Approach #1. We currently use specific dextrans that are amine reactive and contain a flourescent marker such as fluorescein, tetramethylrhodamine, or Cy3.5. The availability of fluorescent dextran conjugates with different sizes and charges will permit us to synthesize a wide variety of prodrugs. These labels are commercially available from Molecular Probes, Eugene, Oreg. and from Pharmacia Amersham, Pistcataway, N.J.

The initial step in this approach will be to generate carbonyls on the dextran that are reactive to a hydrazide containing heterobifunctional linker. The preferred linker of choice is 3-(2-pyridylthio)propionyl hydrazide (PDPH). The generation of hydrazide reactive carbonyls on the dextran is accomplished by gentle oxidation using sodium periodate according to the method of Ranadive, et al. (G. Ranadive, et al., *Nucl. Med. Biol.* 20:719–726, 1993). Briefly, this reaction involves reacting the dextran with 5–10 mM sodium periodate in 100 mM sodium acetate, pH 5.5, for 20–30 minutes in the dark at room temperature. The oxidation reaction is quenched with addition of glycerol to 20 mM final concentration. The dextran is dialyzed against 100 mM sodium acetate, pH 5.5, to remove glycerol and periodate and linker is added to a final concentration of 5–10 mM. This reaction is allowed to proceed for 2 hours at room temperature at which time excess linker is removed from the dextran by applying the mixture to a desalting column such as the Pharmacia PD10.

The desalted, derivatized dextran is then reacted with captopril. The reaction can be monitored by appearance of the leaving group 2-thiopyridine having a characteristic absorbance at 343 nm. After 2 hours incubation at room temperature, excess captopril is removed by desalting on PD10 columns. The amine groups on the dextran are then reacted with the linker sulfo-LC-SMPT. This generates free thiol groups that can then be conjugated directly to botulinum heavy chain via disulfide exchange.

Approach #2. The second approach to conjugating prodrug to heavy chain involves synthesis of prodrug using PDPH-activated amino dextran. Amine-reactive pharmaceutical compounds are added to PDPH-modified amino dextran and allowed to cross-link with the free amine groups present on the dextran. Following removal of excess pharmaceutical by desalting on PD10 columns or extensive dialysis in 25 mM phosphate buffered saline, pH 7.4, the prodrug is added to botulinum heavy chain and the free thiol group(s) on the heavy chain allowed to form disulfide bonds with the thiol reactive portion of the linker PDPH. The reaction is allowed to proceed overnight at 4° C. Excess prodrug is readily separated from the heavy chain-prodrug conjugates by addition of ammonium sulfate to 60% saturation. Under these conditions heavy chain-prodrug and unreacted heavy chain precipitate while the carbohydrate-based prodrug remains in solution.

A second approach to separation of unreacted dextran from botulinum heavy chain can be accomplished by immobilized-metal affinity chromatography (IMAC) according to the method of Schiavo, et al. (G. Schiavo, et al., *Infect. Immun.* 58:4136–4141, 1990). Briefly, chelating Sepharose (Pharmacia) charged with Zn is used to bind the heavy chain of botulinum toxin and heavy chain/polymer constructs. Unreacted dextran is washed from the column with 5–8 column volumes of running buffer and the heavy chain/polymer constructs eluted with 25 mM imidazole.

Preferred therapeutic agents include protease inhibitors. Specific inhibitors include aprotinin, chymostatin, amastatin, bestatin, leupeptin, antipain, trypsin inhibitors, chelating agents such as EDTA, TPEN, o-phenanthroline, and peptide inhibitors of proteases. Peptide inhibitors such as caspase inhibitors (apopain series) which are primarily four and five amino acid inhibitors of caspases are also preferred. Metalloprotease inhibitors such as phosphoramidon, pepstatin A, phebestin, and the TAPI series of matrix metalloprotease inhibitors are also preferred.

The prodrug-heavy chain may be targeted to specific muscle groups by directly injecting the affected muscles. Alternatively, one could deliver the prodrug-heavy chain combination orally.

EXAMPLES

Bacterial Strains and Culturing

The Hall A strain of type A *C. botulinum* was used to produce crystalline type A complex. This strain was originally obtained from Dr. J. H. Mueller at Harvard University and was further screened for high toxin titers at Fort Detrick, Md. by Dr. E. J. Schantz and coworkers. This strain is routinely used for production of type A botulinum toxin due to high toxin titers and the rapid onset of cell lysis (usually within 48 hours).

Stock cultures of *C. botulinum* Hall A were grown statically in 15 ml Hungate tubes containing 10 ml of cooked meat medium +0.3% dextrose (CMM, [Difco Laboratories, Detroit, Mich.]) under an anaerobic atmosphere (80% $N_2$, 10% $CO_2$, 10% $H_2$) at 37° C. for 24 hours and frozen at −20° C. until use. CMM cultures of the Hall A strain give toxin titers in excess of $10^6$ $LD_{50}$/ml in 48–72 hours.

For toxin production, cultures of Hall A were grown statically in 10 liter volumes of toxin production medium (TPM) consisting of 2.0% NZ TT (lot #9NC29) casein hydrolysate (Sheffield Laboratories, Norwich, N.Y.), 1.0% yeast extract (Difco), and 0.5% dextrose, pH 7.3–7.4, for 5–7 days at 37° C. Cultures of Hall A showed heavy growth in this medium during the first 24–48 hours followed by autolysis of the culture which was evident as a clearing and settling over the next 48–120 hours.

Toxin Purification

The production and purification of type A neurotoxin for use as the starting reagent in subsequent chain separations and purifications was successful. As shown in FIG. 1, lanes 1 (unreduced) and 2 (reduced), purification of three batches of type A botulinal neurotoxin having an average specific toxicity of $1.5 \times 10^8$ mouse intraperitoneal lethal doses per mg of protein was successful. Three separate batches of toxin were cultured and purified to homogeneity. Subsequent purification of the component light and heavy chains were performed with yields shown in Table 1.

TABLE 1

Yields of toxin at various stages of purification[1]. (Roman numerals refer to individual purification steps described below.)

| | Batch 1 | Batch 2 | Batch 3 |
|---|---|---|---|
| I. Crude culture[2] | $1.5 \times 10^6$ | $2.0 \times 10^6$ | $3.0 \times 10^6$ |
| II. Toxin complex[1] | 200 | 225 | 275 |
| III. Partially purified neurotoxin[1] | 38 | 47 | 60 |
| IV. Purified neurotoxin[1] | 20 | 23 | 30 |
| V. Light chain[1] | 5 | 5.5 | 9 |
| VI. Heavy chain[1] | 6 | 7 | 11 |

[1]mg of protein,
[2]LD50/ml of crude culture.

We fortuitously determined that toxin production in crude culture could be increased by addition of specific mineral salts to production medium. The addition of magnesium (as magnesium chloride 100 mM final concentration) and calcium carbonate (400 mM final concentration) allowed us to double the amount of toxin produced in culture over the course of this research. This will be extremely important in subsequent scale-ups. As can be seen in Table 1, the amount of toxin complex obtained from Batch 3 vs. Batch 1 did not double as expected based on titers of crude cultures.

Toxin Purification Steps Noted in Table 1

I. Cultures of *C. botulinum* were grown in 10 liter batches of 2% casein hydrolysate, 0.5% dextrose, 0.5% yeast extract, pH 7.4, for 4–5 days at 37° C. Cultures were harvested at this time by addition of 3N $H_2SO_4$ to a final pH of 3.4. Crude toxin precipitated and was collected by centrifugation.

II. Toxin complex was extracted from the acid precipitate by suspending in 200 mM sodium phosphate, pH 6.0. The first extraction was allowed to proceed for 2–3 hours at room temperature. Extracted toxin was separated from cellular debris by centrifugation and the pellet reextracted in similar fashion overnight at 4° C. The extracts were pooled and precipitated with ammonium sulfate (39 g/100 ml). Precipitated extracts were collected by centrifugation and dissolved in 50 mM sodium citrate, pH 5.5. This material was loaded onto DEAE-Sephadex columns equilibrated with the same buffer. Toxin complex eluted essentially unretarded and was pooled and precipitated with ammonium sulfate (39 g/100 ml).

III. Neurotoxin was separated from toxin complex proteins by dialyzing precipitated complex against 3 changes of 20 mM sodium phosphate, pH 7.9. Dialyzed toxin complex was bound to DEAE-Sephadex equilibrated with the same buffer. Partially purified neurotoxin was eluted as the first peak with a 0–300 mM sodium chloride gradient.

IV. Purified neurotoxin was separated from minor amounts of contaminating complex proteins by dialyzing the neurotoxin peak eluted in step III against 20 mM sodium phosphate, pH 7.0, and applying the material to SP-Sephadex equilibrated with the same buffer. Under these conditions contaminating complex proteins did not bind to the matrix. Purified neurotoxin was eluted with a 200 mM sodium chloride step. Neurotoxin recovered from this step was subsequently modified with iodoacetamide thereby alkylating free thiol groups. The rationale for this is described in detail in the next section of this report.

V. Light chain was purified as a by-product of heavy chain purification. Purified neurotoxin was dialyzed against 20 mM sodium borate, 40 mM sodium phosphate, pH 8.4, and applied to QAE-Sephadex equilibrated with the same buffer. After binding neurotoxin to the column, one-half column volume of loading buffer plus 10 mM dithiothreitol (DTT) was applied to the column. A second one-half column volume of loading buffer plus 100 mM DTT and 2 M urea was applied and the column held over night at 4° C. to allow reduction of disulfide bonds. Light chain was eluted with loading buffer plus 10 mM DTT and 2 M urea. Heavy chain and contaminating unnicked neurotoxin were eluted with loading buffer containing 10 mM DTT, 2 M urea, and 500 mM sodium chloride.

VI. Heavy chain containing trace amounts of unnicked neurotoxin was dialyzed against 20 mM sodium phosphate, 5 mM DTT, pH 7.5. The heavy chain was then applied to a column of DEAE-Sephadex equilibrated with the same buffer. Contaminating unnicked neurotoxin was separated from heavy chain by use of a linear 0–600 mM sodium chloride gradient with unnicked neurotoxin eluting at around 100 mM sodium chloride and heavy chain eluting at about 400 mM sodium chloride.

Neurotoxin Modification

Purified type A botulinum heavy chain has six cysteine residues. Of these six thiol groups, two are involved in an intrachain disulfied bond and are not available for reaction with other compounds as the reduced thiols are in such close proximity to each other that they quickly reform a disulfide linkage following removal of the reducing agent (FIG. 2). Treatment of intact neurotoxin with the thiol alkylating agent iodoacetamide yielded a molecule with 0–1.2 free thiols on average as assessed by titration with bis-dithionitrobenzoic acid (Ellman, 1959). This material retained greater than 80% of the starting toxicity as measured by mouse bioassay. Purification of heavy chain was subsequently performed according to the method of Sathyamoorthy and DasGupta (1985) as shown in FIG. 3.

Electrophoresis

Protein samples were examined electrophoretically using the Pharmacia Phastsystem (Pharmacia LKB Inc., Piscataway, N.J.) according to the manufacturers instructions. Precast 12.5% acrylamide gels (Pharmacia) were stained with 0.1% coomassie brilliant blue R250 in 16.7% acetic acid, 41.7% methanol. Gels were destained in 7.5% acetic acid, 25% methanol. Samples for electrophoresis were solubilized in 50 mM Tris-HCl, 5 M urea, 5% SDS, 20% glycerol, pH 6.8. Some samples were reduced by addition of dithiothreitol to a final concentration of 0.5%. All samples for SDS-PAGE were boiled for $\geq 5$ minutes prior to electrophoresis.

Toxin Assays

Toxin titers were estimated in mice using the intravenous method of Boroff and Fleck (1966) and the intraperitoneal method of Schantz and Kautter (1978) in 18–22 g, female, ICR strain mice. Time-to-death values obtained from intravenous titration of type A toxin samples were converted to intraperitoneal $LD_{50}$/ml using a standard curve generated in our laboratory with type A complex. Botulinal toxin for titration was dissolved in 50 mM sodium phosphate, pH 6.8, and then further diluted as required in 30 mM sodium phosphate, 0.2% gelatin, pH 6.4.

Structure of Prodrugs

Polymers selected for reaction with specific linkers included amine reactive dextrans (Molecular Probes, Eugene, Oreg.) having molecular weights of approximately 10 kD and 40 kD. These dextrans had on average 4.8 moles amine per mole of dextran (10 kD) and 6.7 moles amine per mole of dextran (40 kD). The general structures of these compounds are shown in FIG. 4.

Dextran amines were functionalized for conjugation with model inhibitors by addition of the water soluble heterobifunctional linker sulfosuccinimidyl-6-[alpha-methyl-alpha (2-pyridylthio)-toluamido]hexanoate (sulfo-LC-SMPT, FIG. 5).

Figure 6:
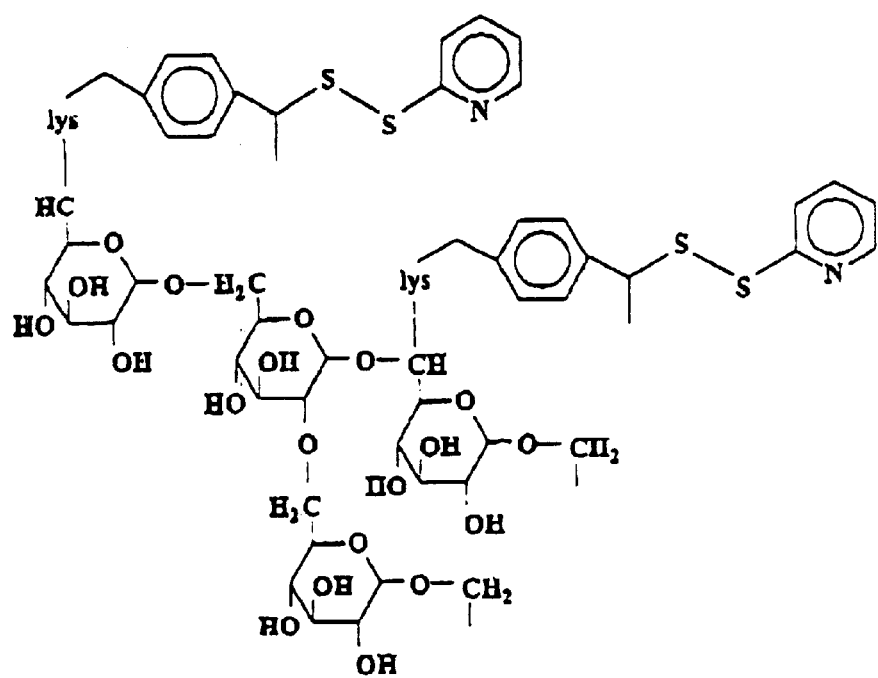
FIG. 6. sulfo-LC-SMPT activated dextran.

Linker was added to amine dextrans at 20:1 molar ratios (20 mole linker:1 mole amine). Linker addition reactions were performed in 100 mM sodium phosphate buffer, pH 9.2, and were allowed to continue for 2 hours at room temperature. This pH favored addition of linker to polymer by reaction of the succinimidyl ester on the linker with the primary amine of the polymer. Unreacted linker was removed by either size exclusion chromatography in the case of the 40 kD dextran on Pharmacia PD10 columns (Pharmacia Biotechnology, Pistcataway, N.J.) equilibrated with 25 mM sodium phosphate buffered saline, pH 7.4, (PBS) or by extensive dialysis vs. PBS in Slidalyzer dialysis cassettes (3.5 kD cutoff, Pierce Biochemical Co., Rockford, Ill.) in the case of the 10 kD dextran. The resulting compounds are shown in FIG. 6.

Figure 7:
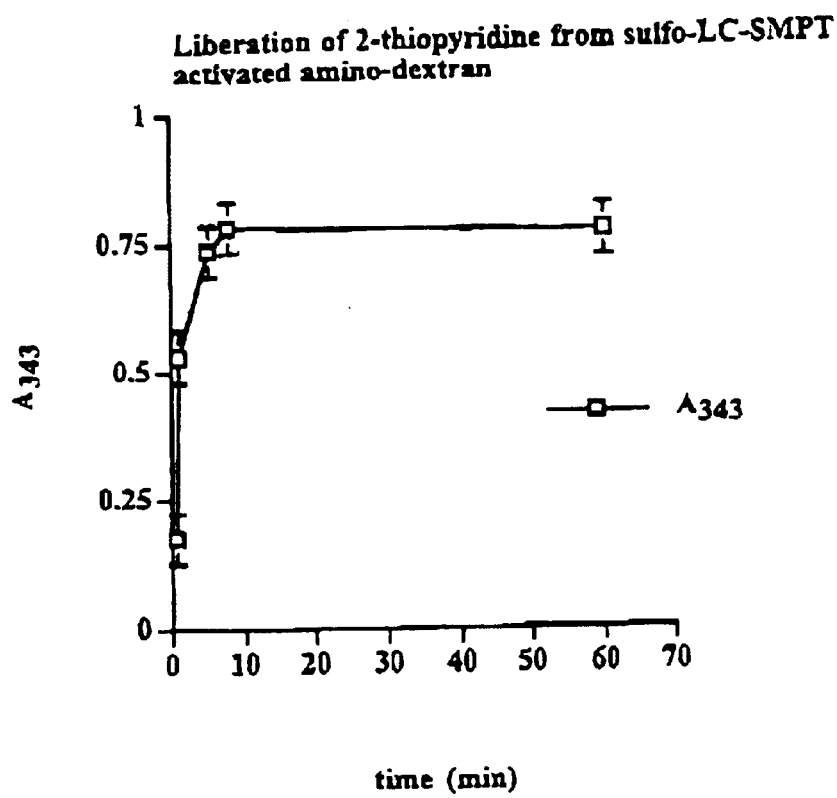
FIG. 7. Release of 2-thiopyridine leaving group from sulfo-LC-SMPT activated dextran.

Linker addition to dextran was confirmed by gentle reduction of functionalized polymer with dithiothreitol. This reaction liberated 2-thiopyridine from the linker which was detected by its characteristic absorbance at 343 nm. In one set of experiments, the final absorbance of 0.77 yielded a molar concentration of the leaving group of 96 $\mu$M indicating that the amine groups or the dextran at a concentration of approximately 750 $\mu$g/ml were over 75% modified by the linker. This is shown in FIG. 7. These reaction kinetics gave nearly identical results with both the 10 kD and the 40 kD amino-dextrans.

We have used the metalloprotease inhibitor captopril as a model pharmaceutical ligand. This ligand has been covalently coupled to linker modified amino dextran via the reactive 2-thiopyridine group. The structure of captopril is shown in FIG. 9.

The reaction kinetics ($A_{343}$ increase) for the displacement of the 2-thiopyridine leaving group from functionalized amino-dextran by captopril were nearly identical to those generated by the reducing agent dithiothreitol indicating that captopril was a good nucleophile and was rapidly bound to the dextran polymer via disulfide bond exchange with the linker. These prodrugs are shown in FIG. 10.

We envision synthesizing prodrugs that contain 5–10× more inhibitor (captopril) than the first generation prodrugs. These prodrugs will have a flourescent label incorporated into them for subsequent in vitro and in vivo visualization and will be conjugated to botulinum heavy chain for targeting and internalization into motor neurons.

We will continue to use dextran based polymers for the synthesis of prodrugs because they are relatively non-toxic and are biologically inert due to the uncommon poly-(-D-1,6-glucose) linkages. They also have low immunogenicity.

Prodrug Assay

We have determined that prodrugs based on the metalloprotease inhibitor captopril described here inhibit angiotensin coverting enzyme (ACE) only when they are released from the dextran carrier by reduction of the disulfide bond. This is advantageous because it sequesters potential therapeutic compounds until they are introduced into the reducing environment of the motor neuron. We used a modification of the assay described by Cushman and Cheung (1971) to measure inhibition of the enzyme by captopril. Cleavage of the substrate by ACE yeilds hippuryl which is soluble in ethyl acetate. Following ethyl acetate extraction of the reactions, the solvent is removed by evaporation and the residue dissolved in water. Hippuryl concentration is measured by absorption at 228 nm.

Figure 8:
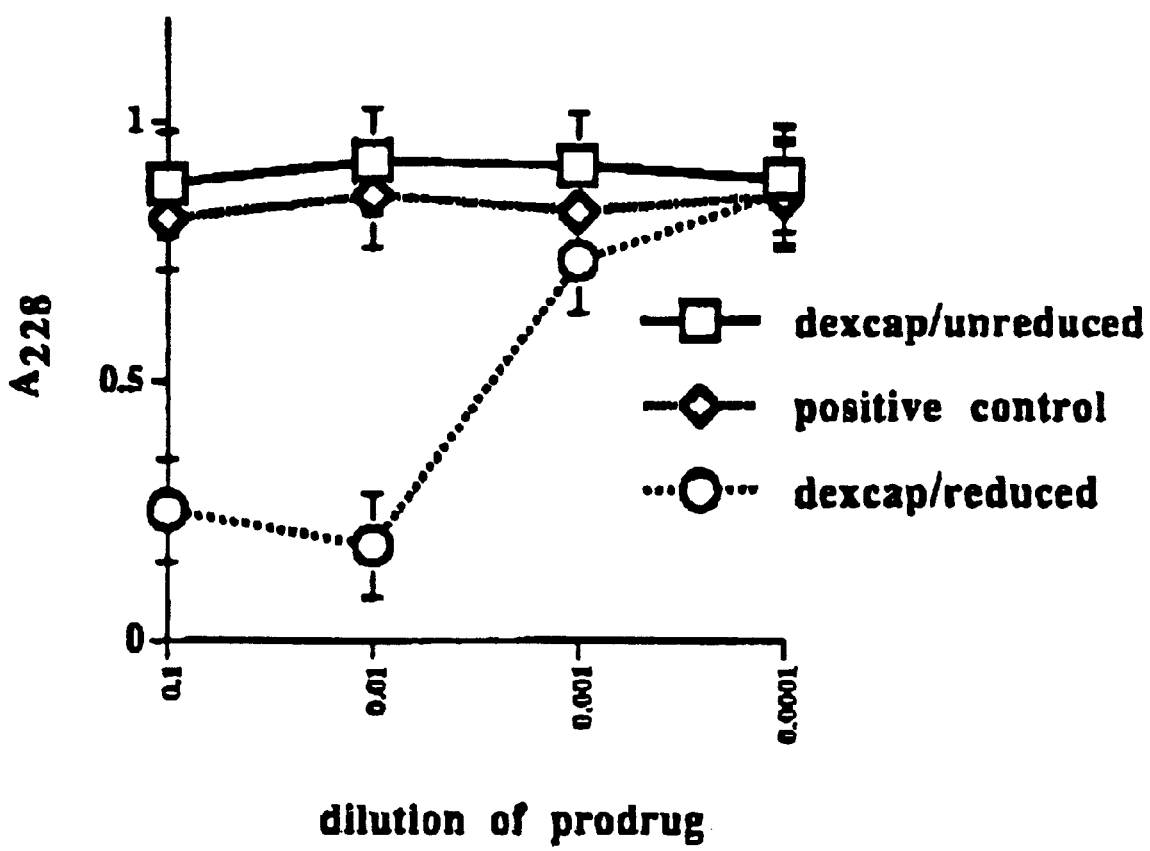
FIG. 8. Inhibition of ACE by reduced prodrug.

Inhibition of ACE was accomplished by addition of known quantities of free captopril. The $IC_{50}$ of captopril for this particular reaction was calculated to be approximately 300 nM. When dextran-captopril conjugates were added to the reaction we did not obtain any inhibition until the disulfide bond between the dextran and captopril was reduced by addition of 2 mM mercaptoethanol. Results of the inhibition studies are shown in FIG. 8. Error bars represent extreme spread of samples tested in triplicate.

Synthesis of Fluorescent Prodrugs

Cyanine dye reagents are useful as markers in biological systems due the fact that they are intensely fluorescent and highly water soluble. We have utilized the Cy 3.5 monofunctional dye (Amersham Pharmacia Biotech, Piscataway, N.J.) as a marker for determining uptake of dextran prodrugs into motor neurons. The Cy 3.5 dye is scarlet fluorescing and is readily detected using standard rhodamine filter sets. The dye is a monofunctional succinimydyl ester that reacts readily with free amine groups. The structure of the dye is shown in FIG. 13.

Synthesis of dextran-based prodrugs (dextran vehicle plus dye) for conjugation to botulinum heavy chain involves two separate linker addition steps. The first step is oxidation of the aminodextran by addition of sodium periodate (10 mM final concentration) to solutions of 10 or 40 kD amminodextran. The reaction is carried out in 100 mM sodium acetate, pH 5.5, for 20 minutes at room temperature. The oxidation reaction is quenched by addition of glycerol to a final concentration of 50 mM. This results in the formation of hydrazide reactive aldehydes and ketones on the aminodextran. Excess periodate and glycerol are removed by extensive dialysis in 100 mM sodium acetate, pH 5.5. These carbonyl groups are reactive with the hydrazide portion of the linker PDPH (3-(2-pyridyidithio)propionyl hydrazide, Pierce Biochemical Co., Rockford, Ill.). PDPH is dissolved in DMSO and added to the dialyzed amino dextran at a final concentration of 10 mM. The reaction is allowed to proceed at room temperature for 2–4 hours.

Figure 14:
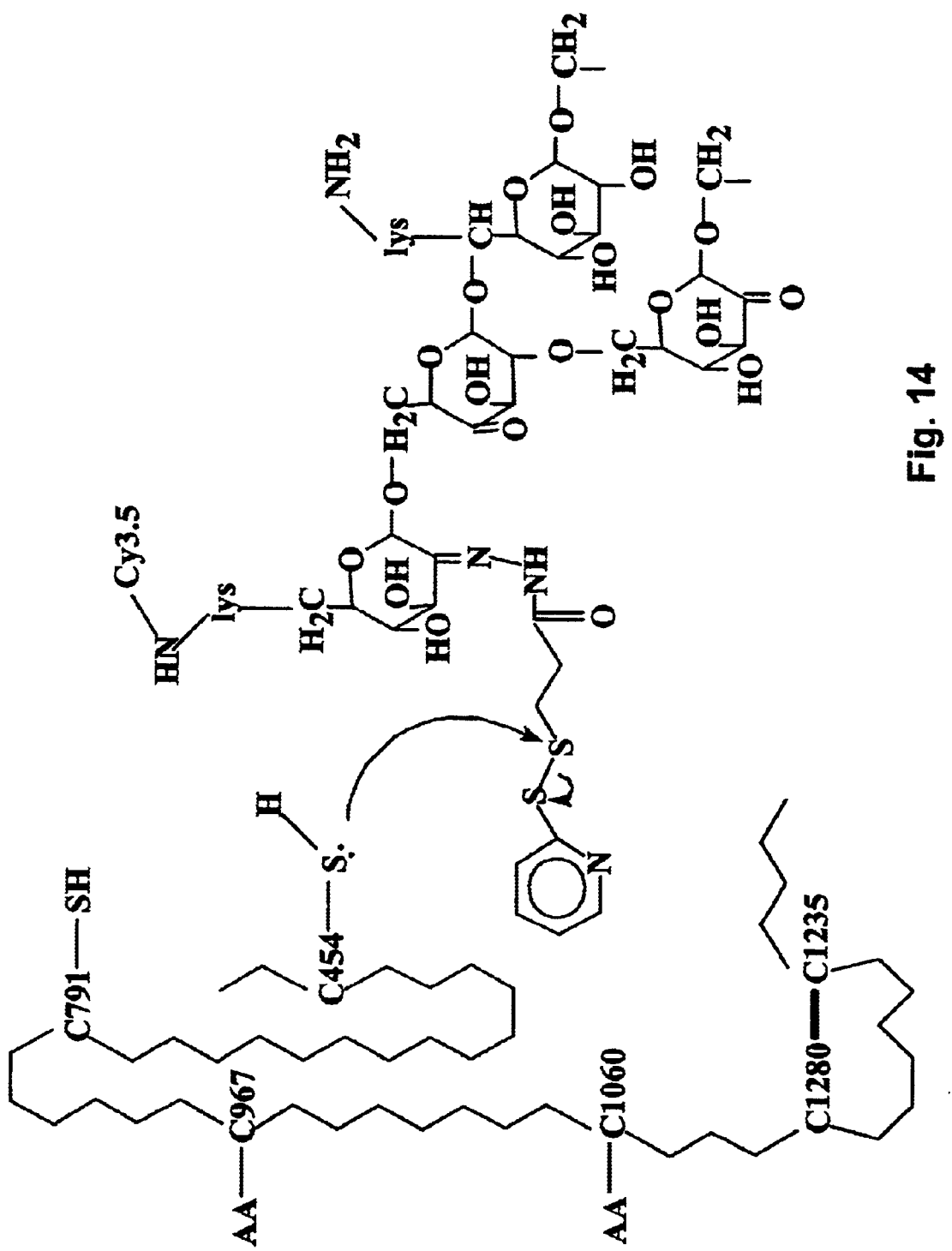
FIG. 14. Reaction of type A botulinum heavy chain with PDPH functionalized Cy 3.5 amino-dextran.

After removal of unreacted linker by size exclusion chromatography or extensive dialysis, the amino dextran plus PDPH is reacted with the Cy 3.5 ester. This reaction adds the dye molecule to the free amine groups present on the dextran. Unreacted dye is removed by either size exclusion chromatography or dialysis and the prodrug conjugated to botulinum heavy chain via the pyridine-2-thione containing portion of the PDPH linker. This reaction scheme is shown in FIG. 14.

Reaction of 40 kD amino dextran prodrug with type A heavy chain results in molecules having molecular weights on SDS-PAGE ranging from 100 kD to approximately 160 kD. The molecules at 100 kD represent unreacted type A heavy chain while the 160 kD molecules represent heavy chain plus one or more dextran prodrugs with a combined molecular weight of approximately 60 kD. These species are all reducible to 100 kD starting heavy chain due to the disulfide bond involved in conjugation.

Conclusions

We have demonstrated that it is possible to chemically synthesize prodrugs consisting of the metalloprotease inhibitor captopril covalently bound to a relatively inert polymeric carrier. Carriers tested to date have included 10 and 40 kD amino dextrans. Additionally, we have successfully modified type A botulinal heavy chain thereby stabilizing the heavy chain relative to the unmodified native heavy chain and allowing us to target conjugation of prodrug to the sulfhydryl originally involved in the disulfide level connecting the heavy and light chains of the toxin.

References

Adler, M., D. MacDonal, L. Sellin, and G. Parker, "Effect of 3,4-diaminopyridine on rat extensor digitorum longus muscle paralyzed by local injection of botulinum neurotoxin," *Toxicon* 34:237–249,1996.

Adler, M., R. Dinterman, and R. Wannemacher, "Protection by the heavy metal chelator N,N,N',N'-tetrakis(2-pyridylmethyl)ethylenediamine (TPEN) against the lethal action of botulinum neurotoxin A and B," *Toxicon* 35:1089–1100,1997.

Boroff, D. A. and U. Fleck, "Statistical analysis of a rapid in vivo method for the titration of the toxin of *Clostridium botulinum*," *J. Bacteriol.* 92:1580–1581, 1966.

Cushman, D. W. and H. S. Cheung, "Spectrophotometric assay and properties of the angiotensin-converting enzyme of rabbit lung," *Biochem. Pharm.,* 20:1637–1648, 1971.

Ellman, G., "Tissue sulfhydryl groups," *Arch. Biochem. Biophys.* 82:70–77, 1959.

Sathyamoorthy, V. and B. DasGupta, "Separation, purification, partial characterization and comparison of the heavy and light chains of botulinum neurotoxin types A, B, and E," *J. Biol. Chem.* 260:10461–10466, 1985.

Schantz, E. and D. Kautter, Standardized assay for Clostridium botulinum toxins,"*J. Assoc. Off. Anal. Chem.* 61:96–99, 1978.

We claim:

1. A method of targeting therapeutic molecules to motor neurons, comprising the steps of:
    (a) synthesizing a prodrug comprising at least one therapeutic molecule covalently bound to a polymeric delivery vehicle wherein the delivery vehicle comprises amine-reactive polymers, and
    (b) conjugating the prodrug to a botulinum neurotoxin heavy chain wherein the conjugation is via a reducible heterobifunctional linker.

2. The method of claim 1 wherein the prodrug comprises at least two copies of a therapeutic molecule.

3. The method of claim 1 wherein the prodrug comprises at least four copies of a therapeutic molecule.

4. The method of claim 1 wherein the prodrug comprises at least two copies of different therapeutic molecules.

5. The method of claim 1 wherein the botulinum neurotoxin heavy chain is obtained via recombinant DNA methods.

6. The method of claim 1 wherein the botulinum neuotoxin heavy chain is obtained from native botulinum toxin.

7. The method of claim 1 wherein the polymeric delivery vehicle comprises a polymer comprising reactive amines and reactive sulfhydryl groups before being bound to the therapeutic molecule via disulfide exchange.

8. The method of claim 1 wherein the therapeutic molecule is captopril.

9. The method of claim 1 wherein the heavy chain is type A botulinum neurotoxin.

10. The method of claim 1 wherein the therapeutic molecule is a metalloprotease inhibitor.

11. The method of claim 1 wherein the heavy chain has been covalently modified.

* * * * *

UNITED STATES PATENT AND TRADEMARK OFFICE
CERTIFICATE OF CORRECTION

PATENT NO. : 6,670,322 B2
DATED : December 30, 2003
INVENTOR(S) : Michael C. Goodnough et al.

It is certified that error appears in the above-identified patent and that said Letters Patent is hereby corrected as shown below:

Column 1,
Line 4, please insert after "STATEMENT REGARDING FEDERALLY SPONSORED RESEARCH OR DEVELOPMENT"
-- This invention was made with United States government support awarded to the following agency: NIH AI42226. The United States has certain rights in this invention. --

Signed and Sealed this

Ninth Day of March, 2004

JON W. DUDAS
*Acting Director of the United States Patent and Trademark Office*